United States Patent [19]

Gmeinder et al.

[11] 4,383,167
[45] May 10, 1983

[54] DRIVE CONTROL CIRCUIT FOR DENTAL TREATMENT INSTRUMENTS

[75] Inventors: Hermann Gmeinder, Warthausen-Oberhöfen; Stefan Beier, Biberach, both of Fed. Rep. of Germany

[73] Assignee: Kaltenbach & Voight GmbH & Co., Biberach, Fed. Rep. of Germany

[21] Appl. No.: 138,705

[22] Filed: Apr. 9, 1980

[30] Foreign Application Priority Data

Apr. 20, 1979 [DE] Fed. Rep. of Germany ......... 291608

[51] Int. Cl.³ .......................... A61C 1/06; H02P 9/44
[52] U.S. Cl. ........................................ 377/2; 318/341; 433/27; 377/45
[58] Field of Search ......... 235/92 CT, 92 EV, 92 PE, 235/92 DE, 92 NT; 433/28, 27; 318/341, 314, 318, 779

[56] References Cited

U.S. PATENT DOCUMENTS 3,843,873 10/1974 Belville .......................... 235/92 EV
4,180,812 12/1979 Kaltenbach ...................... 433/101

FOREIGN PATENT DOCUMENTS 2715798 7/1977 Fed. Rep. of Germany .

Primary Examiner—Felix D. Gruber
Assistant Examiner—D. Rutherford
Attorney, Agent, or Firm—Scully, Scott, Murphy & Presser

[57] ABSTRACT

A circuit arrangement is provided for controlling the drive of dental treatment instruments by means of driving devices associated therewith and the operating data of which are adapted to be fed to a separate forward-/backward counter when the particular treatment instrument is selected for use. A starter switch is connected to the forward/backward counter and is operable, when actuated, to vary the particular stored count of the counter step-wise for the purpose of varying the operating data and for transmission to a control element, for the control thereof, which is associated with the particular treatment instrument. Upon actuation of the starter switch in order to vary the stored count of the forward/backward counter, the counting speed of the counter is increased with increasing actuation time of the starter switch by reason of the fact that the counter receives a number of counter pulses which increase per unit time.

6 Claims, 4 Drawing Figures

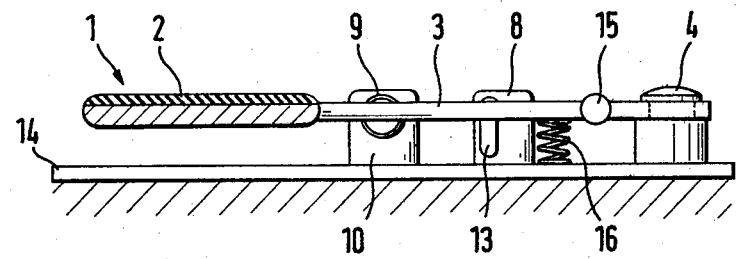
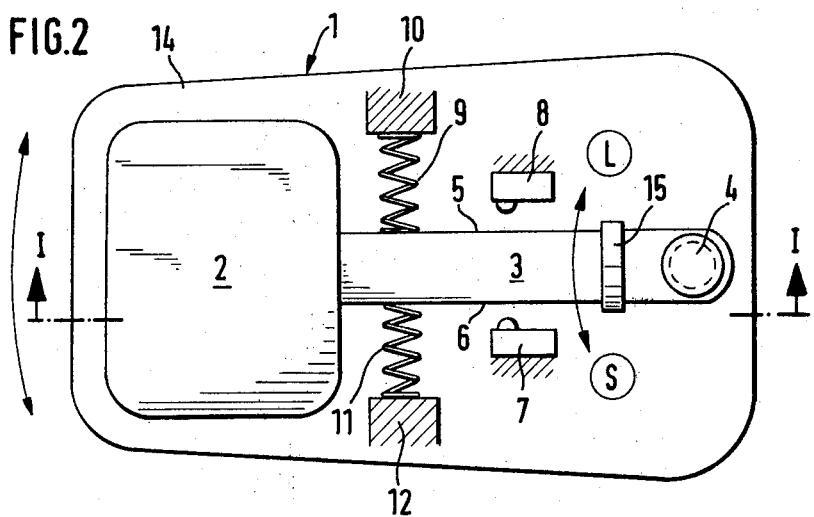

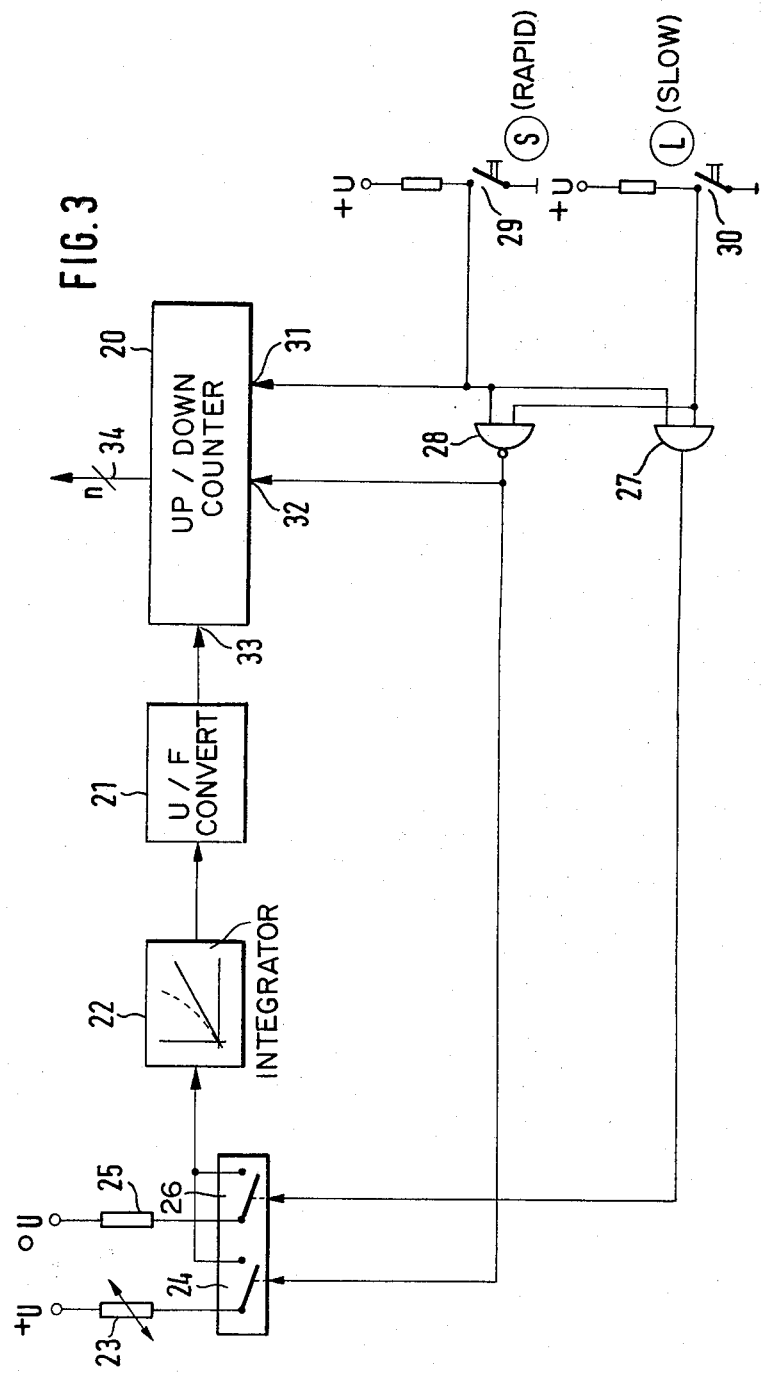

DRIVE CONTROL CIRCUIT FOR DENTAL TREATMENT INSTRUMENTS

This invention relates to a drive control circuit for controlling dental treatment instruments, by means of drive devices associated therewith and the operating data of which are adapted to be fed into a separate forward/backward counter in that case wherein the particular treatment instrument is selected for utilization, whereby due to actuation of a starter switch connected to the forward/backward counter the particular count is variable step-wise for the purpose of a variation of the operating data and is adapted to be transmitted to a control element, for the control thereof, associated with the particular treatment instrument.

A circuit arrangement of the above-described type has already been employed in a dental treatment installation as disclosed in German Offenlegungsschrift No. 27 15 798, which corresponds to U.S. Pat. No. 4,180,812. In the case of this known circuit arrangement, there is employed a specially designed starter switch which, due to lateral deflection of an actuating element about a vertical pivot, permits the actuation of in each particular instance one of two microswitches. On actuation of one microswitch, the provided forward/backward counter will operate in a forward-counting operation and, on actuation of the other microswitch, the appropriate forward/backward counter will operate in the backward counting operation. In this connection, the particular change of the counter position or count of the appropriate counter takes place with a constant counting rate which, however, is also variably adjustable according to a basic adjustment as explained therein.

Although the above-considered, known circuit arrangement operates to a considerable extent satisfactorily in practice, however, a predetermined problematic state has developed. On the one hand, the counting rate of the forward/backward counter is, on variation of the counts corresponding to the operating data, only to be so considerable that adjustment is rendered possible also in only slight amounts and in "aimed" fashion. On the other hand, however, the counting rate of the appropriate counter is to be so considerable that variation of its count about its total counter content takes place within such a period of time which is not felt to be disturbing, i.e. too long, by the operating person. However, the previously considered circuit arrangement is not readily able to satisfy these requirements.

Thus, the invention is based on the problem of providing a circuit arrangement of the type mentioned at the outset, in which it becomes possible in relatively simple manner to vary the count of the provided forward/backward counter both in small amounts and also by large amounts, and in particular about the entire count within a relatively short interval of time which is not yet felt to be disturbing.

According to the invention there is provided a drive control circuit for controlling the drive of dental treatment instruments by means of driving devices associated therewith and the operating data of which are adapted to be fed to a separate forward/backward counter when the particular treatment instrument is selected for use, the circuit comprising:

a forward/backward counter adapted to be fed said operating data;

a starter switch connected to said forward/backward counter and operable, when actuated, to vary the particular count of the counter step-wise for the purpose of varying the operating data and for transmission to a control element, for the control thereof, which is associated with the particular treatment instrument:

and means connected to said forward/backward counter and operable, upon actuation of the starter switch, for the purpose of varying the count of the forward/backward counter, to increase the counting speed or rate of the counter with increasing actuation time of the starter switch by reason of the fact that the counter receives a number of counter pulses which increase per unit time.

The invention involves the advantage that it is achieved in relatively simple manner that both an only slight variation of the count of the provided forward/backward counter and also a variation of the count of the said counter establishing the entire counter capacity of the appropriate counter is made possible within an interval of time which is so short that it is not felt by an operating person to be disturbing. The variation of the counting velocity or rate of the forward/backward counter with increasing actuation time of the starter switch provided can, with this arrangement, take place in dependence on the time either linearly or exponentially.

Preferably, there is connected to a counter pulse input of the forward/backward counter the output of a voltage to frequency converter or transducer which on the output side supplies pulses which are a function of the level of a voltage fed to it in each particular instance at the input side and which at the output side is connected to the output of an integration device or circuit which, as a function of the actuation of the starter switch, transmits an output voltage varying as a function of time to correspond to a predetermined value, the appropriate starter switch being connected to a separate forward/backward counter control input and controlling to be effective either the forward counter operation or the backward counter operation of the forward/backward counter as a function of its switch actuation. Thereby, there is achieved the advantage of an especially slight circuit-technical outlay for varying the counting velocity or rate of the forward/backward counter in the course of variation of a particular counter position or count.

The above-mentioned integration device is expediently connected, during forward counting operation and backward counting operation, with identical integration resistor. This affords the advantage of an especially slight circuit-technical outlay in the case of a so-called upward-integration operation, in which operation is effected both in the case of forward counter operation and the case of backward counter operation.

Expediently, the integration device is adapted to be connected with a separate integration resistor or resistor for the purpose of transfer into a pre-defined starting condition, which is in particular the zero condition of the appropriate integration device. Thereby, there is achieved the advantage that with relatively slight circuit-technical outlay it is possible to operate in a so-called downward integration operation in which the integration device is transferred into a pre-defined starting condition, if it is employed neither for the forward counting operation nor for the backward counting operation.

Expediently, the forward/backward counter has fed to it at a separate counter release input a release signal making possible the carrying into effect of a counting process when the starter switch is in a fixed forward or a fixed backward counter control position. Thereby, there is achieved the advantage that in relatively simple manner pre-defined conditions are created for the carrying into effect of a forward or backward counting operation.

The starter switch is preferably connected with two separate control contacts giving off varying binary signals in the open condition and in the closed condition, at the inputs of two logic elements. Of these logic elements, one is connected at the output side to the actuating input of a switch connecting an integration resistor with the integration device and to the counter release input of the forward/backward counter. The other element is connected at the output side to the actuation input of a further switch connecting a further integration resistor with the integration device. One of the control contacts of the two control contacts provided is additionally connected with the forward/backward counter control input. Thereby, there is achieved the advantage of an especially slight circuit-technical outlay for controlling the forward/backward counter.

The invention will now be described in detail, by way of example only, with reference to the accompanying drawings in which:

FIG. 1 is a section taken on the line I—I of FIG. 2, of a starter switch forming part of a drive control circuit according to the invention;

FIG. 2 is a plan view of the starter switch shown in FIG. 1;

FIG. 3 is a circuit diagram of the drive control circuit according to the invention.

Figure 4:
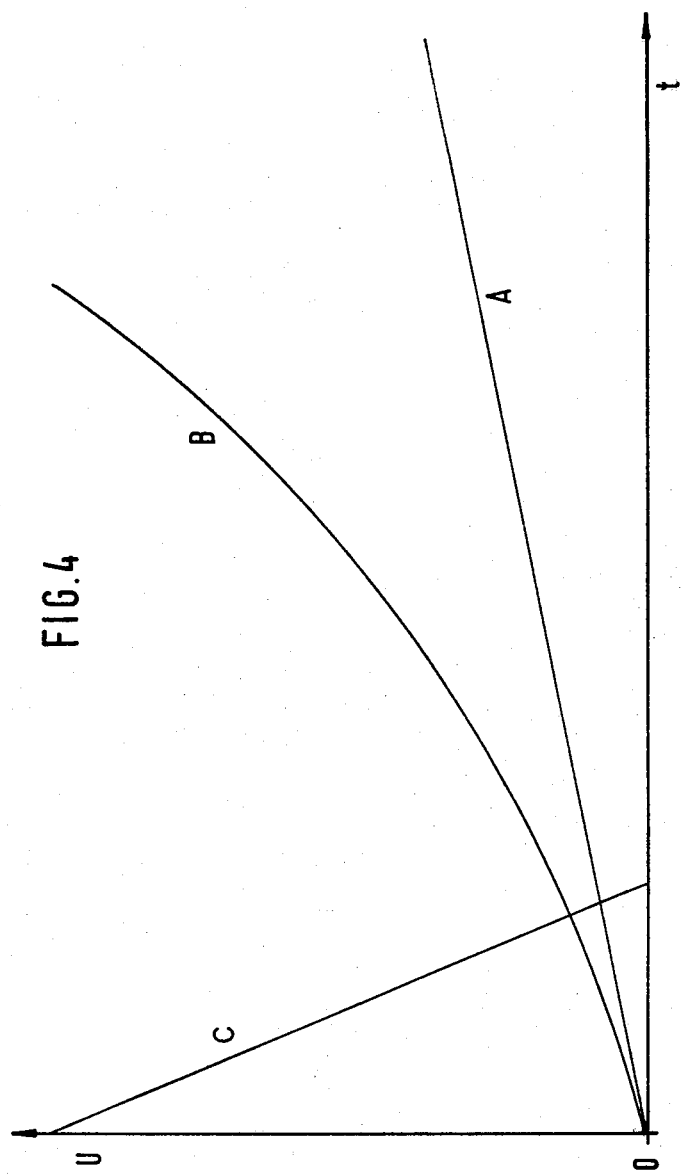
FIG. 4 is a voltage-time diagram of the possible value of output signals of an integration device employed with the drive control circuit.

Referring to FIG. 1, there is shown a starter switch 1 designed as a foot-operated starter switch. The starter switch comprises an actuating pedal 2 pivotal horizontally with a carried arm 3 about a vertical axis provided by a bearing 4, as apparent in particular from FIG. 2. This pivoting movement is adapted to be carried into effect between two extreme positions indicated in FIG. 2 by references L (slow) and S (rapid). In these two extreme positions, the carrier arm 3 bears with a respective one of two contact faces 5, 6 against a corresponding one of two contacts 7, 8 which may be secured, like the bearing 4, to a carrier plate 14. Normally, the carrier arm 3 is retained in its central inoperative position, and for this purpose, springs 9, 11 are supported on bearing blocks 10, 12 and engage the carrier arm 3.

The carrier arm 3 considered hereinabove is furthermore pivotal vertically about an horizontal axis provided by a bearing 15 so as to be able to establish, with a contact member 13, a contact connection to the carrier plate 14. Normally, the plate 2 is retained with the carrier arm 3 in its position shown as the upper position in FIG. 1. A compression spring 16 serves this purpose and presses the carrier arm 3 away from the carrier plate 14.

FIG. 3 shows a possible embodiment of a drive control circuit arrangement according to the invention. This circuit arrangement has a forward/backward counter 20 having a forward/backward counter control input 31, a counter release input 32 and a counter pulse input 33. Via an output 34 possessing n output lines, the forward-backward counter 20 is able to supply signals corresponding to its particular counter position or count.

Connected with its output to the counter pulse input 33 of the counter 20 is a voltage-frequency converter or transducer 21. At its input, the appropriate voltage-frequency transducer 21 is connected to the output of an integration circuit or device 22 which is adapted to be connected at its input side, via first and second separate switches 24, 26, with integration resistors 23 or 25 which with one of their ends may be connected to a voltage source U. The resistor 23 can, as indicated in FIG. 3, be a non-linear resistor.

The actuation inputs of the two switches 24, 26 are connected to the outputs of first and second logic circuits or elements 28,27 (logic switching or logic link-up elements). Thus, the actuation input of the switch 26 is connected to the output of an AND element 27 and the actuation input of the switch 24 is connected to the output of a NAND element 28. The NAND element 28 is furthermore connected at the output side with the counter release input 32 of the forward/backward counter 20.

The AND element 27 and the NAND element 28 each have one input connected jointly to a switch 29 and a further input connected jointly to a switch 30. The two switches 29 and 30 shown in FIG. 3, correspond to the switch contacts 7 and 8 respectively shown in FIGS. 1 and 2. This is indicated in FIG. 3 by the reference numeral "S" or "L" referring to the appropriate switches 29, 30. The aforementioned switch 29 is additionally connected to the forward/backward counter control input 31 of the forward/backward counter 20. With reference to the two switches 29, 30, it should also be stated at this point that the latter, in their open position shown in FIG. 3, in each particular instance supply a binary signal "H" to the devices connected with them. A binary signal "H" is thus supplied by a positive voltage. If, relative thereto, the switches 29, 30 are closed, in each particular instance they supply to the devices connected with them a binary signal "L" which in the present case is constituted by ground potential.

In the following text, it is proceeded from the fact that in the case of the circuit arrangement shown in FIG. 3 the switches 29, 30 are in the open condition. This has the result that the two logic elements 27 and 28 supply a binary signal "H" at the output side, due to which the switch 26 is closed. The binary signal "L" meanwhile fed to the counter release input 32 of the forward/backward counter 20 has the result that the said counter 20 is blocked from performing a counting process. Therewith, it is ensured that, where appropriate, pulses fed to the counter pulse input 33 of the forward/backward counter 20 are not counted by the said counter 20. Such pulses are however normally also not supplied from the voltage-frequency converter or transducer 21 in the case of this switch position of the switch 29, 30, since in fact a control voltage of, by way of example, zero volt is fed to the appropriate transducer 21 from the output of the integration device 22. For supplying the said control voltage, the integration device 22 is forced to actuate in such fashion that the resistor 25 is connected to it via the closed switch 26. The switch 26 is in fact closed (as indicated above) due to the binary signal H transmitted in this condition from the output of the AND element 27. Therewith, the integration device is in a so-called downward-integration operation in which therefore the output voltage supplied by it is conveyed back to a predetermined value of, by way of example, zero volt.

It is now assumed that the switch 29 is closed. The binary signal "L" thereby provided at the forward-/backward counter control input 31 is able to switch the forward/backward counter 20 into its forward counter operation. At the output of the NAND element 28 there then occurs a binary signal "H" which is fed to the counter release input 32 of the counter 20 and thereby releases the said counter 20 for the carrying into effect of a counting process. The counter 20 is now able to count in the forward direction.

The binary signal "H" supplied from the output of the NAND element 28 brings about furthermore the closure of the switch 24, whereby the integration resistor 23 is connected to the integration device 22. Thus, the integration device is in a so-called upward-integration operation in which it supplies an output voltage varying chronologically to correspond to a pre-set value. The output voltage can vary chronologically in linear or exponential fashion. The feed of this output voltage to the input of the voltage-frequency transducer 21 has the result that the said transducer 21 supplies, at the output side, pulses which are merely a function of the level of the voltage fed in each particular instance to it at the input side, to the counter pulse input 33 of the counter 20. The conditions are arranged to be such that there is fed to the counter pulse input 33 of the counter 20, with increasing actuation time of the switch 29, a number of counter pulses which becomes progressively larger per time unit. Expressed in other words, this means that with increasing actuation time of the switch 29 the counting velocity of the counter 20 is increased.

If, in differentiation relative to the above-discussed case of operation, instead of the switch 29 the switch 30 is closed, then the result of this is that from the output of the AND element 27 there is again supplied a binary signal "L" and from the output of the NAND element 28 there is again supplied a binary signal "H". The said binary signal "H" once again brings about the counter release of the counter 20. The binary signal "H" now fed to the forward/backward counter control input 31 of the counter 20 triggers the counter 20 into its backward counting operation. Due to the binary signal "H" supplied from the output of the NAND element 28, the switch 24 is closed, so that the integration device 22 is again connected to the integration resistor 23. Thereby, there again takes place a pulse generation procedure, as previously discussed. Now, however, pulses fed to the counter pulse input 33 of the counter 20 are employed for performing a backward or downward counting process in the said counter 20.

If both the switch 29 and also the switch 30 are again opened, the AND element 27 again supplies a binary signal "H" at the output side, whereas the NAND element 28 supplies a binary signal "L" at the output side. Thereby, then, the switch 26 is closed whereas the switch 24 is opened. Therewith, the integration resistor 25 is connected to the integration device 22 which now however operates in the so-called downward-integration operation at the end of which it is able, at the output side, supply an output voltage of zero volt. This downward-integration process preferably takes place at higher velocity than the previously discussed upward-integration process. The reason for this resides in the fact that it is necessary to ensure that, prior to closure of one of the switches 29, 30, an output voltage of predetermined value is supplied from the output of the integration device 25. In order to be able to differentiate this downward-integration process from the upward-integration process, the binary signal "H" supplied from the output of the AND element 27 can, if appropriate, perform a separate control function in the integration device 22. For this it suffices, on the other hand, to insert the switch 26 into the integration device 22 at an appropriate location.

FIG. 4 shows, in a voltage-time diagram ($U=f(t)$) the values of the voltages (U) adapted to be supplied from the integration device 22 according to FIG. 3, as a function of the time (t). The zone between the curves A and B illustrates the zone to be preferably utilized during upward-integration operation. In this connection, curve A illustrates a linear variation of the voltage U as a function of the time t and curve B illustrates an exponential value of the voltage U as a function of the time t. The curve C shows the value relative to which the voltage U varies as a function of the time t at the output of the integration device 22 according to FIG. 3, during the downward-integration process. In this connection, it is clearly recognized from FIG. 4 that the period of time during which the downward-integration process is developed is substantially shorter than the period of time during which an upward-integration process is developed.

We claim:

1. A drive control circuit for controlling driving of dental treatment instruments by means of driving devices associated therewith, operating data for which is adapted to be fed into a forward/backward counter when a particular treatment instrument is selected for usage, comprising:
   a. a forward/backward counter, having a counting pulse input, and being adapted to be fed with operating data;
   b. a starter switch coupled to said forward/backward counter and being operable, when actuated, to change the count of the forward/backward counter step-wise, for transmission to a control element, which is associated with the particular dental treatment instrument; and
   c. control circuit means coupled between said forward/backward counter and said starter switch and being operable, upon actuation of the starter switch, to change the count in said forward/backward counter at a variable rate by increasing the counting speed of the forward/backward counter with increasing actuation time of the starter switch by increasing the variable rate at which counting pulses are produced at the counting pulse input of said forward/backward counter.

2. A drive control circuit according to claim 1, said drive control circuit including a voltage to frequency converter having an input, an output coupled to the counting pulse input of said forward/backward counter for transmitting pulses thereto with a frequency which is a function of the amplitude of a voltage applied to the input of said voltage to frequency converter; and an integration circuit having an output coupled to the input of said voltage to frequency converter, for transmitting thereto, upon actuation of said starter switch, an output voltage which varies as a function of time; and said starter switch being coupled to a counter direction control input of said forward/backward counter for controlling the forward/backward counter to either count forward or count backward, depending upon actuation of the starter switch.

3. A drive control circuit according to claim 2, said integration circuit having its input coupled to integration resistors during both forward counting and backward counting operations.

4. A drive control circuit according to claim 3, said integration circuit being operable to have its input coupled to a separate integration resistor to define a zero starting condition.

5. A drive control circuit according to claim 2, said forward/backward counter also having a counter release input for receiving a release signal to enable counting thereof in response to forward or backward counter control positions of said starter switch.

6. A drive control circuit according to claim 5, including a first and a second logic circuit, said starter switch including a set of two separate control contacts for supplying binary signals to inputs of said first and second logic circuits, one of said set of two control contacts being coupled to a counter direction control input of said forward/backward counter, a first actuation switch having an actuation input coupled to an output of said first logic circuit which is also coupled to said counter release input of the forward/backward counter, and an integration resistor being operably connected by said first actuation switch to said integration circuit, and a second actuation switch having an actuation input connected to an output of the second logic circuit, and a further resistor being operably connected to said second actuation switch to said integration circuit.

* * * * *